(12) United States Patent
Kobayashi et al.

(10) Patent No.: US 9,365,618 B2
(45) Date of Patent: Jun. 14, 2016

(54) SYNTHETIC PEPTIDE THAT INDUCES EXPRESSION OF TNF RECEPTOR 2 AND USE THEREOF

(75) Inventors: Nahoko Kobayashi, Tsukuba (JP); Tetsuhiko Yoshida, Tsukuba (JP); Mikio Niwa, Tsukuba (JP)

(73) Assignee: TOAGOSEI CO. LTD., Tokyo (JP)

( * ) Notice: Subject to any disclaimer, the term of this patent is extended or adjusted under 35 U.S.C. 154(b) by 138 days.

(21) Appl. No.: 14/114,010

(22) PCT Filed: Apr. 17, 2012

(86) PCT No.: PCT/JP2012/060369
§ 371 (c)(1),
(2), (4) Date: Oct. 25, 2013

(87) PCT Pub. No.: WO2012/150676
PCT Pub. Date: Nov. 8, 2012

(65) Prior Publication Data
US 2014/0051647 A1  Feb. 20, 2014

(30) Foreign Application Priority Data
May 2, 2011 (JP) ................................ 2011-103282

(51) Int. Cl.
| C07K 7/08 | (2006.01) |
| C07K 7/06 | (2006.01) |
| C07K 14/715 | (2006.01) |
| C07K 14/47 | (2006.01) |
| A61K 35/12 | (2015.01) |
| A61K 38/10 | (2006.01) |
| A61K 35/28 | (2015.01) |
| A61K 35/26 | (2015.01) |

(52) U.S. Cl.
CPC ... *C07K 7/08* (2013.01); *C07K 7/06* (2013.01); *C07K 14/4705* (2013.01); *C07K 14/7151* (2013.01); *A61K 35/26* (2013.01); *A61K 35/28* (2013.01); *A61K 38/10* (2013.01); *A61K 2035/126* (2013.01); *C07K 2319/09* (2013.01)

(58) Field of Classification Search
CPC . A61K 35/26; A61K 35/28; A61K 2035/126; A61K 38/10; C07K 14/4705; C07K 14/7151; C07K 2319/09; C07K 7/06; C07K 7/08
See application file for complete search history.

(56) References Cited

U.S. PATENT DOCUMENTS

| 7,531,624 B2 * | 5/2009 | Banes et al. .............. 530/329 |
| 2010/0297758 A1 | 11/2010 | Yoshida et al. |
| 2012/0149053 A1 | 6/2012 | Yoshida et al. |
| 2013/0323776 A1 | 12/2013 | Yoshida et al. |

FOREIGN PATENT DOCUMENTS

| EP | 2236514 A1 | 10/2010 |
| WO | WO 2008/081812 A1 | 7/2008 |
| WO | WO 2009/093692 A1 | 7/2009 |
| WO | 2011/013699 A1 | 2/2011 |

OTHER PUBLICATIONS

UniProt Protein Data Base, LIM domain Kinase 2, protein Accession No. E7EUC1, accessed on Aug. 7, 2014, pp. 1-4.*
Troy R. Torgerson, Regulation of NF-_B, AP-1, NFAT, and STAT1 Nuclear Import in T Lymphocytes by Noninvasive Delivery of Peptide Carrying the Nuclear Localization Sequence of NF-kB p50, J Immunol 1998; 161:6084-6092.*
Luo, D. et al., "Differential Functions of Tumor Necrosis Factor Receptor 1 and 2 Signaling in Ischemia-Mediated Arteriogenesis and Angiogenesis," *The American Journal of Pathology*, Nov. 2006, pp. 1886-1898, vol. 169, No. 5.
Faustman, D. et al., "TNF receptor 2 pathway: drug target for autoimmune diseases," *Nature Reviews Drug Discovery*, Jun. 2010, pp. 482-493, vol. 9.
Luo, Y. et al., "Endothelial-Specific Transgenesis of TNFR2 Promotes Adaptive Arteriogenesis and Angiogenesis" w/ Supplemental Materials, *Arteriosclerosis, Thrombosis, and Vascular Biology Journal of the American Heart Association*, Apr. 15, 2010, pp. 1306-1314; (Supplemental Materials) pp. 1-14.
He, P. et al., "Deletion of tumor necrosis factor death receptor inhibits amyloid β generation and prevents learning and memory deficits in Alzheimer's nice," *The Journal of Cell Biology*, Aug. 27, 2007, pp. 829-841, vol. 178, No. 5.
Hotamisligil, G.S. et al., "Increased Adipose Tissue Expression of Tumor Necrosis Factor-α in Human Obesity and Insulin Resistance," *J. Clin. Invest.*, May 1995, pp. 2409-2415, vol. 95.
Scott, M.S. et al., "Characterization and prediction of protein nucleolar localization and sequences," *Nucleic Acids Research*, Jul. 26, 2010, pp. 7388-7399, vol. 38, No. 21.
Emmott, E. et al., "Nucleolar targeting: the hub of the matter," *EMBO reports*, 2009, pp. 231-238, vol. 10, No. 3.
Fischer, R. et al., "A TNF Receptor 2 Selective Agonist Rescues Human Neurons from Oxidative Stress-Induced Cell Death," *PLoS One*, Nov. 2011, pp. 1-11, vol. 6, No. 11.
Abu-Amer, Y. et al., "Tumor Necrosis Factor Receptors Types 1 and 2 Differentially Regulate Osteoclastogenesis," *The Journal of Biological Chemistry*, Sep. 1, 2000, pp. 27307-27310, vol. 275, No. 35.

(Continued)

*Primary Examiner* — James H Alstrum Acevedo
*Assistant Examiner* — Erinne Dabkowski
(74) *Attorney, Agent, or Firm* — Oliff PLC

(57) ABSTRACT

This invention provides a TNFR2 expression-inducing composition including as an active ingredient a peptide having TNFR2 expression-inducing activity, and a method for producing cells that express TNFR2 selectively by use of the composition. The cell production method provided by this invention includes: culturing at least one species of cells capable of expressing TNF receptor 2, and supplying the cells with a synthetic peptide consisting of a nuclear localization signal sequence (NLS) or a nucleolar localization signal sequence (NoLS) to enhance TNFR2 expression in the cells.

4 Claims, 10 Drawing Sheets

(56) References Cited

OTHER PUBLICATIONS

Kanno, H. et al., "Efficient Neuronal Differentiation of Stem Cells With Intracellular Delivery of a Synthetic Peptide and its Application for Regenerative Therapy," *Yokohama Igaku*, May 30, 2009, pp. 111-115, vol. 60, No. 1-2.

International Search Report issued in International Application No. PCT/JP2012/060369 on May 22, 2012 (with translation).

Kobayashi, Nahoko et al., "Nucleolar Localization Signals of LIM Kinase 2 Function as a Cell-Penetrating Peptide", Protein & Peptide Letters, 2010, vol. 17, pp. 1480-1488.

Al-Lamki, Rafia et al., "Tumor Necrosis Factor Receptor Expression and Signaling in Renal Cell Carcinoma", The American Journal of Pathology, 2010, vol. 177, No. 2, pp. 943-954.

Dec. 3, 2014 Search Report issued in European Application No. 12779331.3.

* cited by examiner

5 μm

5 μm

SEQUENCE LISTING

```
<160> NUMBER OF SEQ ID NOS: 51

<210> SEQ ID NO 1
<211> LENGTH: 8
<212> TYPE: PRT
<213> ORGANISM: Avian infectious bronchitis virus

<400> SEQUENCE: 1

Trp Arg Arg Gln Ala Arg Phe Lys
1               5

<210> SEQ ID NO 2
<211> LENGTH: 19
<212> TYPE: PRT
<213> ORGANISM: Homo sapiens

<400> SEQUENCE: 2

Met Ala Lys Ser Ile Arg Ser Lys His Arg Arg Gln Met Arg Met Met
1               5                   10                  15

Lys Arg Glu

<210> SEQ ID NO 3
<211> LENGTH: 9
<212> TYPE: PRT
<213> ORGANISM: Betanoda virus

<400> SEQUENCE: 3

Arg Arg Arg Ala Asn Asn Arg Arg Arg
1               5

<210> SEQ ID NO 4
<211> LENGTH: 7
<212> TYPE: PRT
<213> ORGANISM: Homo sapiens

<400> SEQUENCE: 4

Ile Met Arg Arg Arg Gly Leu
1               5
```

-continued

<210> SEQ ID NO 5
<211> LENGTH: 16
<212> TYPE: PRT
<213> ORGANISM: herpes simplex virus 1

<400> SEQUENCE: 5

Met Ala Arg Arg Arg Arg His Arg Gly Pro Arg Arg Pro Arg Pro Pro
1               5                   10                  15

<210> SEQ ID NO 6
<211> LENGTH: 8
<212> TYPE: PRT
<213> ORGANISM: Homo sapiens

<400> SEQUENCE: 6

Lys Lys Leu Lys Lys Arg Asn Lys
1               5

<210> SEQ ID NO 7
<211> LENGTH: 7
<212> TYPE: PRT
<213> ORGANISM: Homo sapiens

<400> SEQUENCE: 7

Arg Lys Lys Arg Lys Lys Lys
1               5

<210> SEQ ID NO 8
<211> LENGTH: 15
<212> TYPE: PRT
<213> ORGANISM: Homo sapiens

<400> SEQUENCE: 8

Lys Arg Lys Gly Lys Leu Lys Asn Lys Gly Ser Lys Arg Lys Lys
1               5                   10                  15

<210> SEQ ID NO 9
<211> LENGTH: 18
<212> TYPE: PRT
<213> ORGANISM: Homo sapiens

<400> SEQUENCE: 9

Ser Lys Arg Leu Ser Ser Arg Ala Arg Lys Arg Ala Ala Lys Arg Arg
1               5                   10                  15

Leu Gly

<210> SEQ ID NO 10
<211> LENGTH: 19
<212> TYPE: PRT
<213> ORGANISM: Homo sapiens

<400> SEQUENCE: 10

Gly Arg Cys Arg Arg Leu Ala Asn Phe Gly Pro Arg Lys Arg Arg Arg
1               5                   10                  15

Arg Arg Arg

<210> SEQ ID NO 11
<211> LENGTH: 16
<212> TYPE: PRT
<213> ORGANISM: Marek's disease gammaherpesvirus MKT-1

<400> SEQUENCE: 11

Arg Arg Arg Lys Arg Asn Arg Asp Ala Arg Arg Arg Arg Arg Lys Gln
1               5                   10                  15

```
<210> SEQ ID NO 12
<211> LENGTH: 14
<212> TYPE: PRT
<213> ORGANISM: herpes simplex virus 1

<400> SEQUENCE: 12

Lys Arg Pro Arg Arg Arg Pro Ser Arg Pro Phe Arg Lys Pro
1               5                   10

<210> SEQ ID NO 13
<211> LENGTH: 17
<212> TYPE: PRT
<213> ORGANISM: Homo sapiens

<400> SEQUENCE: 13

Met Gln Arg Lys Pro Thr Ile Arg Arg Lys Asn Leu Arg Leu Arg Arg
1               5                   10                  15

Lys

<210> SEQ ID NO 14
<211> LENGTH: 11
<212> TYPE: PRT
<213> ORGANISM: Homo sapiens

<400> SEQUENCE: 14

Pro Arg Arg Gly Ala Gln Leu Arg Arg Pro Arg
1               5                   10

<210> SEQ ID NO 15
<211> LENGTH: 13
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 15

Lys Lys Arg Thr Leu Arg Lys Asn Asp Arg Lys Lys Arg
1               5                   10

<210> SEQ ID NO 16
<211> LENGTH: 13
<212> TYPE: PRT
<213> ORGANISM: Rattus norvegicus
<220> FEATURE:
<221> NAME/KEY: MOD_RES
<222> LOCATION: (4)..(4)
<223> OTHER INFORMATION: PHOSPHORYLATION

<400> SEQUENCE: 16

Lys Lys Arg Thr Leu Arg Lys Ser Asp Arg Lys Lys Arg
1               5                   10

<210> SEQ ID NO 17
<211> LENGTH: 13
<212> TYPE: PRT
<213> ORGANISM: Homo sapiens

<400> SEQUENCE: 17

Lys Lys Arg Thr Leu Arg Lys Asn Asp Arg Lys Lys Arg
1               5                   10

<210> SEQ ID NO 18
```

```
<211> LENGTH: 17
<212> TYPE: PRT
<213> ORGANISM: Homo sapiens

<400> SEQUENCE: 18

Asp Lys Pro Asn Ser Lys Arg Ser Arg Gln Arg Asn Asn Glu Asn
1               5                   10                  15

Arg

<210> SEQ ID NO 19
<211> LENGTH: 12
<212> TYPE: PRT
<213> ORGANISM: Human immunodeficiency virus

<400> SEQUENCE: 19

Arg Lys Lys Arg Arg Gln Arg Arg Arg Ala His Gln
1               5                   10

<210> SEQ ID NO 20
<211> LENGTH: 14
<212> TYPE: PRT
<213> ORGANISM: Homo sapiens

<400> SEQUENCE: 20

Gly Arg Pro Arg Arg Gly Phe Lys Thr Arg Arg Thr Gln Lys
1               5                   10

<210> SEQ ID NO 21
<211> LENGTH: 13
<212> TYPE: PRT
<213> ORGANISM: Mus musculus

<400> SEQUENCE: 21

Gln Pro Arg Gln Arg Arg Gln Leu Lys Gln Ser Pro Gly
1               5                   10

<210> SEQ ID NO 22
<211> LENGTH: 14
<212> TYPE: PRT
<213> ORGANISM: Homo sapiens

<400> SEQUENCE: 22

Arg Ser Arg Lys Tyr Thr Ser Trp Tyr Val Ala Leu Lys Arg
1               5                   10

<210> SEQ ID NO 23
<211> LENGTH: 12
<212> TYPE: PRT
<213> ORGANISM: Human adenovirus

<400> SEQUENCE: 23

Arg Leu Pro Val Arg Arg Arg Arg Arg Arg Val Pro
1               5                   10

<210> SEQ ID NO 24
<211> LENGTH: 14
<212> TYPE: PRT
<213> ORGANISM: Semliki Forest virus

<400> SEQUENCE: 24

Lys Lys Lys Asp Lys Gln Ala Asp Lys Lys Lys Lys Lys Pro
1               5                   10

<210> SEQ ID NO 25
```

```
<211> LENGTH: 18
<212> TYPE: PRT
<213> ORGANISM: Homo sapiens

<400> SEQUENCE: 25

Ser Lys Arg Leu Ser Ser Arg Ala Arg Lys Arg Ala Ala Lys Arg Arg
1               5                   10                  15

Leu Gly

<210> SEQ ID NO 26
<211> LENGTH: 18
<212> TYPE: PRT
<213> ORGANISM: Homo sapiens

<400> SEQUENCE: 26

Phe Lys Arg Lys His Lys Lys Asp Ile Ser Gln Asn Lys Arg Ala Val
1               5                   10                  15

Arg Arg

<210> SEQ ID NO 27
<211> LENGTH: 20
<212> TYPE: PRT
<213> ORGANISM: Homo sapiens

<400> SEQUENCE: 27

Thr Pro Lys Glu Lys Lys Ala Lys Thr Ser Lys Lys Lys Lys Arg Ser
1               5                   10                  15

Lys Ala Lys Ala
            20

<210> SEQ ID NO 28
<211> LENGTH: 20
<212> TYPE: PRT
<213> ORGANISM: Homo sapiens

<400> SEQUENCE: 28

Gly Lys Gly Val Gln Pro Arg Arg Arg Gln Lys Gln Ser Pro Asp
1               5                   10                  15

Asn Leu Glu Pro
            20

<210> SEQ ID NO 29
<211> LENGTH: 21
<212> TYPE: PRT
<213> ORGANISM: Homo sapiens

<400> SEQUENCE: 29

Gly Lys Lys Lys Lys Gly Lys Pro Gly Lys Arg Arg Glu Gln Glu Lys
1               5                   10                  15

Lys Lys Arg Arg Thr
            20

<210> SEQ ID NO 30
<211> LENGTH: 21
<212> TYPE: PRT
<213> ORGANISM: Homo sapiens

<400> SEQUENCE: 30

Arg Arg Ile Leu Pro Lys Pro Thr Arg Lys Ser Arg Thr Lys Asn Lys
1               5                   10                  15

Gln Lys Arg Pro Arg
            20
```

<210> SEQ ID NO 31
<211> LENGTH: 6
<212> TYPE: PRT
<213> ORGANISM: Homo sapiens

<400> SEQUENCE: 31

Leu Lys Arg Arg Arg Ala
1               5

<210> SEQ ID NO 32
<211> LENGTH: 17
<212> TYPE: PRT
<213> ORGANISM: Homo sapiens

<400> SEQUENCE: 32

Gln Leu Arg Arg Pro Arg His Ser His Pro Thr Arg Ala Arg Arg Cys
1               5                   10                  15

Pro

<210> SEQ ID NO 33
<211> LENGTH: 20
<212> TYPE: PRT
<213> ORGANISM: Homo sapiens

<400> SEQUENCE: 33

Ser Lys Lys Thr Asn Arg Gly Ser Gln Leu His Lys Tyr Tyr Met Lys
1               5                   10                  15

Arg Arg Thr Leu
            20

<210> SEQ ID NO 34
<211> LENGTH: 8
<212> TYPE: PRT
<213> ORGANISM: Homo sapiens

<400> SEQUENCE: 34

Lys Lys Leu Lys Lys Arg Asn Lys
1               5

<210> SEQ ID NO 35
<211> LENGTH: 7
<212> TYPE: PRT
<213> ORGANISM: Homo sapiens

<400> SEQUENCE: 35

Arg Lys Lys Arg Lys Lys Lys
1               5

<210> SEQ ID NO 36
<211> LENGTH: 8
<212> TYPE: PRT
<213> ORGANISM: Homo sapiens

<400> SEQUENCE: 36

Arg Arg Tyr Lys Arg His Tyr Lys
1               5

<210> SEQ ID NO 37
<211> LENGTH: 19
<212> TYPE: PRT
<213> ORGANISM: Homo sapiens

<400> SEQUENCE: 37

-continued

Gly Arg Cys Arg Arg Leu Ala Asn Phe Pro Gly Arg Lys Arg Arg
1               5                   10                  15

Arg Arg Arg

<210> SEQ ID NO 38
<211> LENGTH: 14
<212> TYPE: PRT
<213> ORGANISM: Homo sapiens

<400> SEQUENCE: 38

Lys Ser Lys Lys Lys Lys Lys Lys Lys Lys Gln Gly Glu
1               5                   10

<210> SEQ ID NO 39
<211> LENGTH: 13
<212> TYPE: PRT
<213> ORGANISM: Homo sapiens

<400> SEQUENCE: 39

Lys Gln Ile Lys Lys Lys Lys Ala Arg Arg Glu Thr
1               5                   10

<210> SEQ ID NO 40
<211> LENGTH: 17
<212> TYPE: PRT
<213> ORGANISM: Homo sapiens

<400> SEQUENCE: 40

Arg Arg Ala Ala Thr Glu Asn Ile Pro Val Val Arg Arg Pro Asp Arg
1               5                   10                  15

Lys

<210> SEQ ID NO 41
<211> LENGTH: 18
<212> TYPE: PRT
<213> ORGANISM: Homo sapiens

<400> SEQUENCE: 41

Lys Lys Lys Gln Gly Cys Gln Arg Glu Asn Glu Thr Leu Ile Gln Arg
1               5                   10                  15

Arg Lys

<210> SEQ ID NO 42
<211> LENGTH: 18
<212> TYPE: PRT
<213> ORGANISM: Homo sapiens

<400> SEQUENCE: 42

Arg Lys His Asp Asp Cys Pro Asn Lys Tyr Gly Glu Lys Lys Thr Lys
1               5                   10                  15

Glu Lys

<210> SEQ ID NO 43
<211> LENGTH: 17
<212> TYPE: PRT
<213> ORGANISM: Homo sapiens

<400> SEQUENCE: 43

Lys Lys Lys Met Lys Lys His Lys Asn Lys Ser Glu Ala Lys Lys Arg
1               5                   10                  15

Lys

```
<210> SEQ ID NO 44
<211> LENGTH: 19
<212> TYPE: PRT
<213> ORGANISM: Homo sapiens

<400> SEQUENCE: 44

Arg Leu Lys Ile Lys Gly Gln Arg Lys Ile Tyr Gln Ala Asn Gly Lys
1               5                   10                  15

Gln Lys Lys

<210> SEQ ID NO 45
<211> LENGTH: 10
<212> TYPE: PRT
<213> ORGANISM: Homo sapiens

<400> SEQUENCE: 45

Gln Asp Leu Trp Gln Trp Arg Lys Ser Leu
1               5                   10

<210> SEQ ID NO 46
<211> LENGTH: 15
<212> TYPE: PRT
<213> ORGANISM: Homo sapiens

<400> SEQUENCE: 46

Met Pro Arg Ala Pro Arg Cys Arg Ala Val Arg Ser Leu Leu Arg
1               5                   10                  15

<210> SEQ ID NO 47
<211> LENGTH: 9
<212> TYPE: PRT
<213> ORGANISM: Homo sapiens

<400> SEQUENCE: 47

Asn Lys Lys Lys Lys Pro Lys Lys Glu
1               5

<210> SEQ ID NO 48
<211> LENGTH: 14
<212> TYPE: PRT
<213> ORGANISM: Homo sapiens

<400> SEQUENCE: 48

Arg Pro Gln Arg Arg Asn Arg Ser Arg Arg Arg Arg Asn Arg
1               5                   10

<210> SEQ ID NO 49
<211> LENGTH: 13
<212> TYPE: PRT
<213> ORGANISM: Homo sapiens

<400> SEQUENCE: 49

Asp Arg Pro Leu Val Phe Phe Asp Leu Lys Ile Asp Asn
1               5                   10

<210> SEQ ID NO 50
<211> LENGTH: 11
<212> TYPE: PRT
<213> ORGANISM: Homo sapiens

<400> SEQUENCE: 50

Lys Gln Ala Trp Lys Gln Lys Trp Arg Lys Lys
1               5                   10
```

```
<210> SEQ ID NO 51
<211> LENGTH: 7
<212> TYPE: PRT
<213> ORGANISM: Homo sapiens

<400> SEQUENCE: 51

His Arg Lys Gly Arg Arg Arg
1               5
```

SYNTHETIC PEPTIDE THAT INDUCES EXPRESSION OF TNF RECEPTOR 2 AND USE THEREOF

TECHNICAL FIELD

The present invention relates to a synthetic peptide capable of inducing certain cells to selectively express TNF receptor 2 as well as use thereof. In particular, it relates to a composition to induce expression of TNF receptor 2 with the composition comprising the peptide as an active ingredient, and also to a method for producing cells selectively expressing TNF receptor 2 by use of the peptide.

The present application claims priority based on Japanese Patent Application No. 2011-103282 filed on May 2, 2011, and its entire contents are incorporated herein by reference.

BACKGROUND ART

Tumor necrosis factors generally called as TNF (typically three types, namely TNF-α, TNF-β (LT-α), LT-β) are cytokines that are produced primarily in immune cells. TNF-α being representative thereof is produced mainly in macrophages and shows various physiological activities such as small thrombi formation and apoptosis induction, etc. Excessive production (expression) of TNF-α is known to bring on diseases such as rheumatoid arthritis and the like.

Not limited to these, physiological activities by TNF-α are deeply involved in the maintenance of homeostasis in living organisms. Thus, an increase or a suppression of TNF-α production may influence living organisms in various ways. For example, in addition to that TNF-α by itself is able to suppress insulin secretion similarly to interleukin 1 (IL-1) and interferon γ (IFNγ), it is known that a combination of these physiologically active substances is toxic to pancreatic β cells and considered to be related to β-cell apoptosis in type 1 diabetes. It has also been reported that TNF gene polymorphism linked to high production of TNF-α is involved in type 1 diabetes. TNF-α is considered to be involved also in the development of type 2 diabetes (insulin-resistant diabetes). For instance, the relationship between TNF-α expression in mast cells and insulin resistance has been discussed (Non-Patent Document 5). It has been also reported that an anti-TNF antibody injected to neutralize TNF-α can relieve insulin resistance and that in TNF receptor-deficient obese mice and TNF-deficient obese mice, levels of insulin resistance were mild, etc., suggesting that a TNF (typically TNF-α) is significantly involved in the development of insulin resistance and determining its level.

Known TNF-α-binding receptors include TNF receptor 1 (tumor necrosis factor receptor 1, or also "TNFR1" hereinafter) having a molecular weight of about 55 kDa as well as TNF receptor 2 (tumor necrosis factor receptor 2, or also "TNFR2" hereinafter) having a molecular weight of about 75 kDa (e.g. Non-Patent Document 1).

Between these, TNFR1 having a presence of a region referred to as a death domain is locally expressed in various cells constituting a living organism while TNFR2 free of a death domain is an inducible receptor with a significant expression caused by a certain stimulus being found primarily in immune cells (e.g. Non-Patent Document 2). It has been known that depending on to which of the two types of receptors TNF-α binds, the physiological activity induced by the TNF-α varies. For example, TNF-α binding to TNFR1 causes activation of caspases and induces cell apoptosis (cell death) through a signal transduction pathway involving several caspases.

CITATION LIST

Non Patent Literature

[Non-Patent Document 1] The American Journal of Pathology, vol. 169(5), 2006, pp. 1886-1898
[Non-Patent Document 2] Nature Reviews Drug Discovery, vol. 9, 2010, pp. 482-493
[Non-Patent Document 3] Arteriosclerosis, Thrombosis, and Vascular Biology, vol. 30, 2010, pp. 1307-1314
[Non-Patent Document 4] The Journal of Cell Biology, vol. 178(5), 2007, pp. 829-841
[Non-Patent Document 5] The Journal of Clinical Investigation, vol. 95, 1995, pp. 2409-2415
[Non-Patent Document 6] Nucleic Acids Research, vol. 38(21), 2010, pp. 7388-7399
[Non-Patent Document 7] EMBO reports, vol. 10(3), 2009, pp. 231-238
[Non-Patent Document 8] PLoS ONE, [online] vol. 6(11), January 2011, e27621, <www.plosone.org/article/info%3Adoi%2F10.1371%2Fjournal.pone.0027621>

SUMMARY OF INVENTION

As compared to elucidation of signal transduction pathways activated by TNF (mainly TNF-α) binding to TNFR1 and physiological activities induced thereby, it has been a slow process to elucidate signal transduction pathways activated by TNF binding to TNFR2 and physiological activities induced thereby. This type of research has grown in recent years, gradually revealing the roles and functions that TNFR2 serves in various physiological activities induced by TNF For example, Non-Patent Document 3 and Non-Patent Document 1 listed above state that by allowing high and specific expression of TNFR2 in endothelial cells, angiogenesis and arteriogenesis are enhanced. In other words, specific expression or activation of TNFR2 in prescribed tissue (or cells) is effective in treating vascular diseases (vascular disorders) such as coronary artery diseases (disorders) and peripheral vascular diseases (disorders).

Non-Patent Document 4 indicates that in experiments using TNFR1-knockout transgenic mice, amyloid β production was inhibited and amyloid β plaque formation was reduced in the brains. This indicates that similarly to direct suppression of TNFR1 expression, specific TNFR2 expression in prescribed tissue (or cells) can competitively inhibit TNF (mainly TNF-α) binding to TNFR1, raising expectations for contributing to treatment or improvement of Alzheimer's disease. By competitive inhibition of TNF (mainly TNF-α) binding to TNFR1, relief of insulin resistance is also expected.

Non-Patent Document 8 further shows that in experiments using human dopaminergic neuronal cells, selective expression of TNFR2 can rescue differentiated neurons from cell death subsequent to a toxic exposure. In other words, selective activation of TNFR2 is expected to contribute to treatment or improvement of neurodegenerative diseases such as Parkinson's disease.

The present invention was thus made to provide a material or a means to control (or adjust) expression (or activation) of TNFR2 to thereby contribute to treatment or improvement of vascular diseases described earlier as well as Alzheimer's disease and Parkinson's disease; or to provide a material (typically reagents) and/or a means that can be used in research and development fields devoted to improve such diseases (disorders).

In order to accomplish the objectives, the present invention provides a composition as described below. In particular, disclosed herein is a composition to be supplied to at least one species of cells (a cell line) capable of expressing TNF receptor 2 in order to enhance expression of the TNF receptor 2 in the cells, with the TNF receptor 2 expression-inducing composition (or "TNRF2 expression-inducing composition" hereinafter) comprising a synthetic peptide consisting of a nuclear localization signal sequence (NLS) or a nucleolar localization signal sequence (NoLS), and a pharmaceutically acceptable carrier.

Herein, the term "cells capable of expressing TNF receptor 2 (TNFR2)" refers to cells in which steady or temporal TNFR2 expression is observed in vivo or in vitro. For example, immune cells of human or other mammal origin are typical examples of cells capable of expressing TNF receptor 2 (TNFR2) which is a TNF receptor of approximately 75 kDa that is clearly distinct from TNFR1 by the absence of the death domain.

The present inventors have completed this invention upon discovering that by supplying cells potentially capable of expressing TNFR2 (or "target TNFR2-expressing cells" hereinafter) with a relatively short-chain synthetic peptide consisting of an amino acid sequence that constitute a signal sequence for nuclear localization contained in various proteins that are biologically synthesized in the cells and subsequently transported to nuclei, that is a "nuclear localization signal (NLS)", or a signal sequence that allows further transport (localization) of the proteins to nucleoli within nuclei, that is a "nucleolar localization signal (NoLS)", expression of TNF receptor 2 (TNFR2) is greatly increased in the cells.

In other words, by supplying prescribed target TNFR2-expressing cells with a "TNFR2 expression-inducing peptide" as a primary ingredient in the composition disclosed herein, in particular, a synthetic peptide consisting of an NLS (or simply a "synthetic NLS peptide" hereinafter) or a synthetic peptide consisting of an NoLS (or simply a "synthetic NoLS peptide" hereinafter) (e.g. by adding a composition or a peptide according to the present invention to a culture medium in which prescribed target TNFR2-expressing cells are being cultured), expression of TNFR2 can be stimulated or its yield can be increased in the target TNFR2-expressing cells supplied with the synthetic peptide.

Accordingly, the cell production method disclosed herein can contribute to treatment or improvement of various diseases and disorders (e.g. various vascular diseases, Alzheimer's disease, Parkinson's disease) associated with TNFR2 expression and TNF binding to the receptor. The cell production method disclosed herein can be practiced preferably in research and development fields devoted to improvement of such diseases (disorders) (e.g. fields related to medicine, pharmaceuticals, genetics, biochemistry, and biology. The same applies hereinafter).

In a preferable embodiment, the composition disclosed herein comprises a synthetic peptide consisting of an amino acid sequence represented by any one of SEQ ID NOs: 1 to 51.

Each of the amino acid sequences represented by SEQ ID NOs: 1 to 51 is an NLS or NoLS (Note: a sequence capable of serving as an NoLS can typically function also as an NLS) whose sequence is known (e.g. see Non-Patent Documents 6 and 7 above), and preferably constitutes a synthetic NLS peptide or a synthetic NoLS peptide in the composition disclosed herein. The synthetic peptide consisting of an amino acid sequence represented by one of the SEQ ID NOs encompasses a synthetic peptide consisting of the original amino acid sequence (unmodified sequence) identified by the SEQ ID NO as well as a synthetic peptide consisting of a modified amino acid sequence resulting from a partial modification of the original amino acid sequence, with the synthetic peptide being capable of inducing TNFR2 expression similarly to the unmodified sequence.

To accomplish the objectives, the present invention also provides a method for producing cells that express TNF receptor 2 selectively (i.e. preferentially or specifically) between TNF receptor 1 (TNFR1) and TNF receptor 2 (TNFR2).

This method is characterized by comprising culturing at least one species of cells capable of expressing TNF receptor 2, and supplying the cells with a synthetic peptide consisting of a nuclear localization signal sequence (NLS) or a nucleolar localization signal sequence (NoLS) to enhance expression of TNF receptor 2 in the cells.

According to a cell production method comprising these steps, a treatment as simple as supplying target TNFR2-expressing cells of interest that are being cultured with a synthetic NLS peptide or a synthetic NoLS peptide can enhance TNFR2 expression in the cells selectively (i.e. preferentially or specifically relative to TNFR1). Thus, the cell production method disclosed herein can contribute to treatment or improvement of various diseases and disorders associated with TNFR2 and TNF binding to the receptor (e.g. various vascular diseases, Alzheimer's disease, Parkinson's disease). It can also provide a material that can be used in research and development fields devoted to improvement of such diseases (disorders).

In a preferable embodiment, the cell production method disclosed herein is characterized by culturing at least one species of immune cells as the cells capable of expressing TNF receptor 2 (the target TNFR2-expressing cells).

By providing immune cells (e.g. thymus cells, i.e., various lymphocytes) expressing high levels of TNFR2, it can contribute to treatment or improvement of immunological diseases (e.g. autoimmune diseases such as rheumatoid arthritis, etc.) brought on in part by a signal transduced from TNF (typically TNF-α) binding to TNFR1. It can also provide a material that can be used in research and development fields devoted to improvement of such immunological diseases (immunological disorders).

In a preferable embodiment, the cell production method disclosed herein is characterized by culturing at least one species of neural cells as the cells capable of expressing TNF receptor 2 (the target TNFR2-expressing cells).

By providing neural cells (e.g. neuroblasts) expressing high levels of TNFR2, it can contribute to treatment or improvement of neurological diseases (e.g. neurodegenerative diseases such as Parkinson's disease, etc.) brought on in part by a signal transduced from TNF (typically TNF-α) binding to TNFR1. It can also provide a material that can be used in research and development fields devoted to improvement of such neurological diseases (neurological disorders).

In another preferable embodiment, the cell production method disclosed herein is characterized by use of a synthetic peptide consisting of an amino acid sequence represented by any one of SEQ ID NOs: 1 to 51, as the synthetic peptide. NLS and NoLS amino acid sequences identified by SEQ ID NOs: 1 to 51 are preferable for use because they are constituted with a relatively small number of amino acid residues and can be easily obtained by chemical synthesis. The TNFR2 expression-inducing peptide encompasses the synthetic peptide consisting of the original amino acid sequence (unmodified sequence) identified by any one of the SEQ ID NOs as well as a synthetic peptide consisting of a modified amino acid sequence resulting from a partial modification of the original amino acid sequence.

The present invention also provides an artificially designed polynucleotide that does not exist in nature, with the polynucleotide comprising a nucleotide sequence encoding a TNFR2 expression-inducing synthetic peptide disclosed herein, and/or a nucleotide sequence complimentary thereto (e.g. a polynucleotide essentially consisting of these sequences).

Preferable polynucleotides include a polynucleotide comprising a nucleotide sequence encoding the amino acid sequence represented by any one of SEQ ID NOs: 1 to 51, and/or a nucleotide sequence complimentary thereto (e.g. a polynucleotide essentially consisting of these sequences).

EMBODIMENTS OF INVENTION

Figure 1:
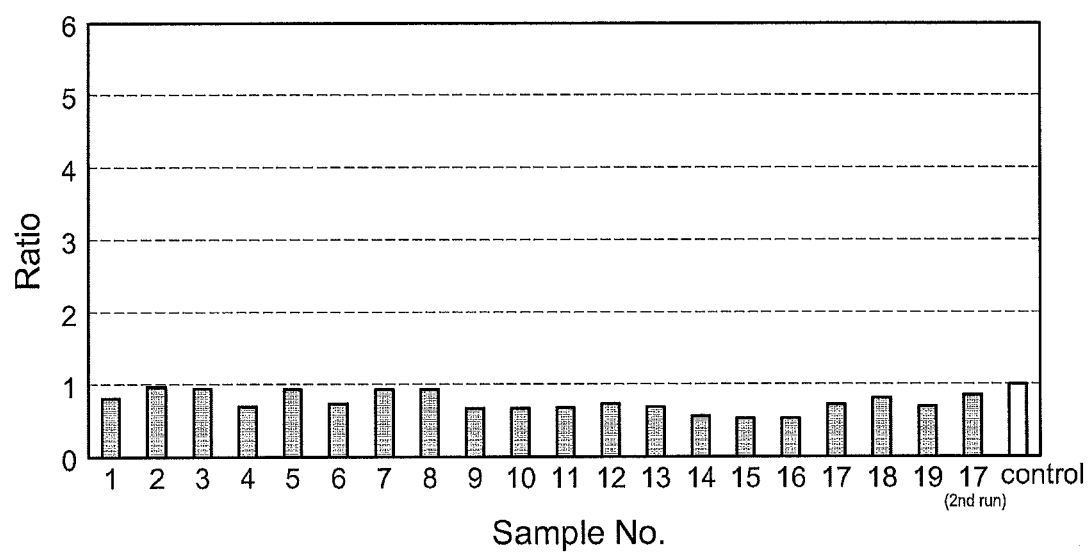
FIG. 1 shows a graph plotting the results of testing cultured cells of a control and each sample group for the TNFR1 expression levels (relative fluorescence intensity values with the control set as 1) based on a fluorescent antibody technique using an anti-TNFR1 polyclonal antibody (primary antibody) and a fluorescently labeled secondary antibody.

Preferred embodiments of the present invention are described below. Note that technical matters other than those matters particularly mentioned in the present description (e.g., the primary structure and chain length of a TNFR2-inducing synthetic peptide disclosed herein) which are required for carrying out the present invention (e.g., general matters relating to chemical peptide synthesis, cell cultivation, and preparation of a pharmaceutical composition containing a peptide) are matters of design variation that could be apprehended by a person skilled in the art based on prior art in such fields as cell engineering, medicine, pharmacology, organic chemistry, biochemistry, genetic engineering, protein engineering, molecular biology, genetics, and the like. The present invention can be practiced based on the technical details disclosed in the present description and on common general technical knowledge in the pertinent fields. In the following description, amino acids are indicated by single-letter designations (in sequence listings, by three-letter designations) in accordance with the nomenclature for amino acids set forth in the IUPAC-IUB guidelines.

The present description incorporates by reference the entire contents of all the documents cited herein.

In the present description, "synthetic peptide" refers to a peptide fragment that is manufactured by artificial chemical synthesis or biosynthesis (i.e., genetic engineering-based production) and can stably exist in a certain composition (e.g., a TNF receptor 2 expression-inducing composition).

In this description, the term "peptide" refers to an amino acid polymer having a plurality of peptide bonds, and is not limited by the number of amino acid residues included in the peptide chain, with the term typically referring to one having a relatively small molecular weight with no more than 50 (e.g. no more than 30) amino acid residues in total.

In this description, unless specified otherwise, the term "amino acid residue" includes the N-terminal amino acid and the C-terminal amino acid of a peptide chain.

In this description, the term "modified amino acid sequence resulting from a partial modification" relative to a selected amino acid sequence refers to an amino acid sequence formed by substituting, deleting and/or adding (inserting) one or several (e.g. two or three) amino acid residues without impairing functions (typically an ability to induce TNFR2 expression) of the selected amino acid sequence. Typical examples of the modified amino acid sequence referred to in the present description include a sequence generated by conservative amino acid replacement where one or several (typically two or three) amino acid residues are conservatively substituted (e.g., a basic amino acid residue is substituted with a different basic amino acid residue; e.g. mutual substitution between a lysine residue and an arginine residue), a sequence corresponding to a selected amino acid sequence with addition (insertion) or deletion of one or several (typically two or three) amino acid residues, and the like. Thus, the TNFR2 expression-inducing peptide disclosed herein encompass synthetic peptides consisting of amino acid sequences identical to the amino acid sequences of the respective SEQ ID NOs described below (i.e. the respective amino acid sequences listed in Table 1 and Table 2) as well as a synthetic peptide consisting of an amino acid sequence resulting from substitution (e.g. the conservative substitution) or addition of one or several (typically two or three) amino acid residues in the amino acid sequence of each SEQ ID NO and showing comparable TNFR2 expression-inducing activity.

In this description, the term "polynucleotide" refers to a polymer (nucleic acids) in which several nucleotides are linked by phosphodiester bonds, but not limited by the number of nucleotides. As used herein, the term 'polynucleotide' encompasses DNA fragments and RNA fragments of various lengths. "Artificially designed polynucleotide" refers to a polynucleotide whose chain (whole length) does not exist by itself in nature and that is manufactured artificially by chemical synthesis or biosynthesis (i.e., genetic engineering-based production).

The TNFR2 expression-inducing composition disclosed herein comprises, as an active ingredient, a peptide consisting of an NLS or NoLS that has been discovered for the first time by the present inventors to have an ability to induce TNFR2 expression (or an ability to activate TNFR2 expression) in certain cells.

As described above, the TNFR2 expression-inducing peptide disclosed herein can be considered as a synthetic peptide that does not exist in nature in view that it consists solely of an amino acid sequence that functions as an NLS or NoLS (typically, an NoLS functions as an NLS; in other words, some NLS are considered as NoLS as well).

Table 1, Table 2 and Sequence Listing show preferable examples of an amino acid sequence constituting the TNFR2 expression-inducing peptide disclosed herein. These amino acid sequences listed are all known as NLS or NoLS, and their data can be obtained, for example, from the database of protein amino acid sequences provided by NCBI (National Center for Biotechnology Information).

TABLE 1

| SEQ ID No. | Amino acid sequence | Protein/Peptide |
|---|---|---|
| 1 | WRRQARFK | IBV N protein |
| 2 | MAKSIRSKHRRQMRMMKRE | ApLLP |
| 3 | RRRANNRRR | GGNNV α protein |
| 4 | IMRRRGL | Angiogenin |
| 5 | MARRRHRGPRRPRPP | HSV type1 γ protein |
| 6 | KKLKKRNK | MDM2 |
| 7 | RKKRKKK | NIK |
| 8 | KRKGKLKNKGSKRKK | Nuclear VCP-like protein |
| 9 | SKRLSSRARKRAAKRRLG | p120 |
| 10 | GRCRRLANFGPRKRRRRRR | HIC p40 |
| 11 | RRRKRNRDARRRRRKQ | MDV MEQ protein |
| 12 | KRPRRRPSRPFRKP | HVS ORF57 |
| 13 | MQRKPTIRRKNLRLRRK | Survivin-delta Ex3 |
| 14 | PRRGAQLRRPR | P14ARF |
| 15 | KKRpTLRKNDRKKR | human LIMK2 (phosphorylated) |
| 16 | KKRpTLRKSDRKKR | rat LIMK2 (phosphorylated) |
| 17 | KKRTLRKNDRKKR | human LIMK2 |

TABLE 1-continued

| SEQ ID No. | Amino acid sequence | Protein/Peptide |
|---|---|---|
| 18 | DKPNSKRSRRQRNNENR | NP_937862 ING1b(NoLS-1) |
| 19 | RKKRRQRRRAHQ | HIV-1 TAT |

(NP_xxxxxx in the table is an accession number in NCBI Reference Sequences.)

TABLE 2

| SEQ ID No. | Amino acid sequence | Protein/Peptide |
|---|---|---|
| 20 | GRPRRGEKTRRTQK | FGF3 |
| 21 | QPRQRRQKKQSPG | FGF3 |
| 22 | RSRKYTSWYVALKR | FGF2 |
| 23 | RLPVRRRRRRVP | Adenovirus PTP1,2 |
| 24 | KKKDKQADKKKKKP | Semliki Forestvirus capsid protein |
| 25 | SKRLSSRARKRAAKRRLG | NP_006161 NOP2 |
| 26 | FKRKHKKDISQNKRAVRR | NP_005336 HSPA1A |
| 27 | TPKEKKAKTSKKKKRSKAKA | NP_937862 ING1b(NoLS-2) |
| 28 | GKGVQPRRRRQKQSPDNLEP | NP_005238 FGF3 |
| 29 | GKKKKGKPGKRREQEKKKRRT | NP_945316 PTHLH |
| 30 | RRILPKPTRKSRTKNKQKRPR | NP_001002 RPS7 |
| 31 | LKRRRA | NP_001034800 DEDD |
| 32 | QLRRPRHSHPTRARRCP | NP_478102 CDKN2A |
| 33 | SKKTNRGSQLHKYYMKRRTL | NP_477352 PI4KA |
| 34 | KKLKKRNK | NP_002383 MDM2 |
| 35 | RKKRKKK | NP_003945 MAP3K14 |
| 36 | RRYKRHYK | NP_078908 SAP30L |
| 37 | GRCRRLANFPGRKRRRRRR | NP_951038 MDFIC |
| 38 | KSKKKKKKKKQGE | NP_848927 MTDH |
| 39 | KQIKKKKKARRET | NP_848927 MTDH |
| 40 | RRAATENIPVVRRPDRK | NP_078805 CDC73 |
| 41 | KKKQGCQRENETLIQRRK | NP_078805 CDC73 |
| 42 | RKHDDCPNKYGEKKTKEK | NP_060239 G2E3 |
| 43 | KKKMKKHKNKSEAKKRK | NP_055318 UTP20 |
| 44 | RLKIKGQRKIYQANGKQKK | AAB60345 L1 ORF2 |
| 45 | QDLWQWRKSL | NP_002511 NPM1 |
| 46 | MPRAPRCRAVRSLLR | NP_937983 TERT |
| 47 | NKKKKPKKE | NP_003277 TOP1 |
| 48 | RPQRRNRSRRRRNR | NP_004851 FXR2 |
| 49 | DRPLVFFDLKIDN | NP_150241 PML |

TABLE 2-continued

| SEQ ID No. | Amino acid sequence | Protein/Peptide |
|---|---|---|
| 50 | KQAWKQKWRKK | NP_004251 RECQL4 |
| 51 | HRKGRRR | NP_068778 PPP1R11 |

(NP_xxxxxx in the table is an accession number in NCBI Reference Sequences.)

The amino acid sequence of SEQ ID NO: 1, for instance, corresponds to a nucleolar localization sequence consisting of 8 total amino acid residues contained in N protein (nucleocapsid protein) of IBV (avian infectious bronchitis virus).

The amino acid sequence of SEQ ID NO: 2 corresponds to an NoLS consisting of 19 total amino acid residues originating from a species of nucleolar protein (ApLLP).

The amino acid sequence of SEQ ID NO: 3 corresponds to an NoLS consisting of 9 total amino acid residues originating from GGNNVα which is a protein of a betanodavirus The amino acid sequence of SEQ ID NO: 4 corresponds to an NoLS consisting of 7 total amino acid residues originating from angiogenin which is a vascular endothelial growth factor.

The amino acid sequence of SEQ ID NO: 5 corresponds to an NoLS consisting of 16 total amino acid residues originating from a protein (γ(1)34.5) of HSV-1 (herpes simplex virus 1).

The amino acid sequence of SEQ ID NO: 6 corresponds to an NoLS consisting of 8 total amino acid residues originating from MDM2 which is a nuclear phosphoprotein and forms a complex with p53 tumor suppressor protein.

The amino acid sequence of SEQ ID NO: 7 corresponds to an NoLS consisting of 7 total amino acid residues originating from NF-κB-inducing kinase (NIK).

The amino acid sequence of SEQ ID NO: 8 corresponds to an NoLS consisting of 15 total amino acid residues originating from nuclear VCP-like protein.

The amino acid sequence of SEQ ID NO: 9 corresponds to an NoLS consisting of 18 total amino acid residues originating from p120 which is a nucleolar protein.

The amino acid sequence of SEQ ID NO: 10 corresponds to an NoLS consisting of 19 total amino acid residues originating from p40 protein of HIC (a human I-mfa domain-containing protein).

The amino acid sequence of SEQ ID NO: 11 corresponds to an NoLS consisting of 16 total amino acid residues originating from MEQ protein of MDV (Marek's disease virus).

The amino acid sequence of SEQ ID NO: 12 corresponds to an NoLS consisting of 14 total amino acid residues originating from ORF57 protein of HVS (herpesvirus saimiri).

The amino acid sequence of SEQ ID NO: 13 corresponds to an NoLS consisting of 17 total amino acid residues originating from Survivin-deltaEx3 which is an apoptosis-suppressing protein.

The amino acid sequence of SEQ ID NO: 14 corresponds to an NoLS consisting of 11 total amino acid residues originating from p14ARF which is a tumor suppressor protein.

The amino acid sequences of SEQ ID NOs: 15 to 17 each correspond to an NoLS consisting of 13 total amino acid residues originating from LIM kinase 2 (LIMK2) which is a protein kinase involved in intracellular signaling and is present in human or rat endothelial cells.

The amino acid sequence of SEQ ID NO: 18 corresponds to an NoLS consisting of 17 total amino acid residues originating from ING1b which is a product of the family of ING tumor suppressor genes.

The amino acid sequence of SEQ ID NO: 19 corresponds to an NLS consisting of 12 total amino acid residues originating from the protein transduction domain of HIV (human immunodeficiency virus) TAT.

The amino acid sequences of SEQ ID NOs: 20 and 21 each correspond to an NoLS consisting of 14 total amino acid residues originating from FGF3 (fibroblast growth factor-3).

The amino acid sequence of SEQ ID NO: 22 corresponds to an NoLS consisting of 14 total amino acid residues originating from FGF2 (fibroblast growth factor-2).

For other data such as the origins (species of organisms) of the respective amino acid sequences (NLS and/or NoLS) of SEQ ID NOs: 23 to 51, RefSeq provided by NCBI and like database shall be consulted.

As for the TNFR2 expression-inducing peptide disclosed herein, a preferable peptide has at least one amidated amino acid residue. Amidation of a carboxyl group in an amino acid residue (typically the C-terminal amino acid residue of the peptide chain) may increase the structural stability (e.g., protease resistance) of the synthetic peptide.

The present inventors completed this invention upon discovering that when a peptide consisting of an amino acid sequence known as an NLS or NoLS such as the amino acid sequences represented by the respective SEQ ID NOs was synthesized and supplied to target TNFR2-expressing cells (e.g. thymus cells) that were being cultured, the synthetic peptide was able to permeate cellular membranes of the target cells highly efficiently and allowed selective (specific) expression of TNFR2.

In a synthetic peptide to be used, the peptide chain is constituted with suitably at most 50 amino acid residues in total, desirably at most 30, for instance, preferably 6 or more, but 25 or less. The number of amino acid residues in a general NLS or NoLS is within these ranges.

Such a short chain peptide can be easily prepared by chemical synthesis, thus the TNFR2 expression-inducing peptide can be readily provided. Although no particular limitation is imposed on the conformation (spatial structure) of the peptide for as long as the TNFR2 expression capability is exhibited in the environment employed (in vitro or in vivo), a linear or helical conformation is preferred from the standpoint of the less likelihood of becoming an immunogen (antigen). Peptides of these conformations are less likely to form epitopes. From these standpoints, as the TNFR2 expression-inducing peptide applied to the TNFR2 expression-inducing composition, a linear peptide with a relatively low molecular weight (typically with at most 30 (especially at most 25) amino acid residues) is preferred.

It is noted that in the TNFR2 expression-inducing peptide disclosed herein, all amino acid residues are preferably L-amino acids while for as long as the TNFR2 expression-inducing activity is not lost, part or all of the amino acid residues may be substituted with D-amino acids.

The TNFR2 expression-inducing peptide disclosed herein can be easily manufactured according to conventional chemical synthesis methodologies. For instance, any of conventional solid-phase and liquid-phase synthetic methods can be employed. A preferable solid-phase synthetic method uses Boc (t-butyloxycarbonyl) or Fmoc (9-fluorenylmethoxycarbonyl) as the protecting group for the amino group.

For the TNFR2 expression-inducing peptide disclosed herein, a peptide chain having a desired amino acid sequence and a portion with modification (e.g., C-terminal amidation) can be synthesized by solid-phase synthesis using a commercial peptide synthesizer (which is, for instance, available from PerSeptive Biosystems, Applied Biosystems, etc.).

Alternatively, the TNFR2 expression-inducing peptide may be biosynthesized based on genetic engineering techniques. In particular, a polynucleotide (typically a DNA strand) is synthesized so as to have a nucleotide sequence (including the ATG initiation codon) encoding the amino acid sequence of the desired TNFR2 expression-inducing peptide. Then, in accordance with the host cells, a recombinant vector is constructed so as to have an expression gene construct composed of the synthesized polynucleotide (DNA) and various regulatory elements (including promoters, ribosome binding sites, terminators, enhancers, and various cis-elements which control the expression level) to allow expression of the amino acid sequence within the host cells.

By an ordinary technique, this recombinant vector is inserted into prescribed host cells (e.g., yeasts, insect cells), and the host cells, or tissue or a masse containing these cells are cultured under specific conditions. In this way, the target peptide can be expressed and produced intracellularly. The target TNFR2 expression-inducing peptide can be obtained by isolating the peptide from the host cells (from the culture medium if secreted) and purifying it.

Methods hitherto used in the art may be directly employed without modification for constructing the recombinant vector and introducing the constructed recombinant vector into the host cell. Because such methods themselves are not distinctive to the present invention, detailed description is omitted.

For example, a fusion protein expression system may be employed to allow efficient large-scale production in host cells. In particular, a gene (DNA) coding for the amino acid sequence of the TNFR2 expression-inducing peptide of interest is chemically synthesized, and the synthesized gene is introduced to a preferred site on a fusion protein expression vector (e.g. GST (glutathione S-transferase) fusion protein expression vectors such as the pET series available from Novagen as well as the pGEX series available from Amersham Bioscience). Host cells (typically, *Escherichia coli*) are then transformed by the vector. The resulting transformant is cultured to produce the target fusion protein. This protein is then extracted and purified. Subsequently, the purified fusion protein is cleaved with a specific enzyme (protease), and the liberated target peptide fragments (the designed TNFR2 expression-inducing peptide) are collected by a method such as affinity chromatography. The TNFR2 expression-inducing peptide of the present invention can be produced by using such a fusion protein expression system heretofore known (e.g., the GST/His system available from Amersham Bioscience may be used).

Alternatively, the target polypeptide may be synthesized in vitro by constructing a template DNA for a cell-free protein synthesis system (i.e., a synthesized gene fragment having a nucleotide sequence that codes for the amino acid sequence of the TNFR2 expression-inducing peptide), and employing a cell-free protein synthesis system with use of various compounds (e.g., ATP, RNA polymerase, amino acids, etc.) required for the peptide synthesis. For information concerning cell-free protein synthesis systems, reference may be made to, for example, Shimizu et al., Nature Biotechnology, 19, 751-755 (2001), and Madin et al., Proc. Natl. Acad. Sci. USA, 97(2), 559-564 (2000). Based on the technology described in these articles, many corporations have been conducting contract manufacturing of polypeptides at the time when this application was filed. Also, wheat germ cell-free protein synthesis kits (such as PROTEIOS™ available from Toyobo Co., Ltd. of Japan) are commercially available.

By a heretofore known method, can be easily produced (synthesized) a single-stranded or double-stranded polynucleotide containing a nucleotide sequence encoding the TNFR2 expression-inducing peptide disclosed herein and/or a nucleotide sequence complementary thereto. In other words, by selecting a codon corresponding to the respective amino acid residues constituting the designed amino acid sequence, a nucleotide sequence corresponding to the amino acid sequence of the TNFR2 expression-inducing peptide can be easily determined and provided. Once the nucleotide sequence is determined, by utilizing a DNA synthesizer, etc., can be easily obtained a polynucleotide (single strand) corresponding to the desired nucleotide sequence. Furthermore, the target double-stranded DNA can be obtained by using the resulting single-stranded DNA as a template and employing various enzymatic synthetic methods (typically PCR).

The polynucleotide provided by the present invention may be in the form of DNA or RNA (mRNA, etc.). The DNA can be provided as a double strand or a single strand. When it is provided as a single strand, it may be a coding strand (sense strand) or an anticoding strand (anti-sense strand) complementary thereto.

The polynucleotide provided by the present invention can be used as a material for constructing a recombinant DNA (expression cassette) for producing the TNFR2 expression-inducing peptide in various host cells or in a cell-free protein synthesis system.

The TNFR2 expression-inducing peptide disclosed herein can act on at least one species of target TNFR2-expressing cells (typically immune cells or neural cells, e.g. thymus cells and neuroblasts) to induce selective expression of TNFR2 or to enhance TNFR2 expression in the cells. Hence, it can be used as an active ingredient in a TNFR2 expression-inducing composition (pharmaceutical composition). The TNFR2 expression-inducing peptide contained can be a salt as far as the TNFR2 expression-inducing activity is not impaired. For example, it is possible to use an acid salt of the peptide, which can be obtained by adding a commonly used inorganic or organic acid in accordance with an ordinary technique. Alternatively, while the TNFR2 expression-inducing activity is obtained, a different type of salt (e.g., a metal salt) can be used. The "peptide" described in this description and in claims encompasses such salts.

The TNFR2 expression-inducing composition disclosed herein may contain various pharmaceutically (medically) acceptable carriers in accordance with the application form as far as the TNFR2 expression-inducing peptide as the active ingredient is maintained active in expressing TNFR2. Carriers generally used as diluents or excipients in peptide medications are preferred. Although it may suitably vary depending on the intended purpose and form of the composition disclosed herein (i.e., a TNFR2 expression-inducing agent), typical examples include water, physiological buffers and various organic solvents. The carrier may be an aqueous alcohol (ethanol or the like) solution at an appropriate concentration, glycerol, or non-drying oil such as olive oil. Alternatively, it may be a liposome. Examples of secondary ingredients that may be contained in the TNFR2 expression-inducing composition include various fillers, bulking agents, binders, wetting agents, surfactants, dyes, fragrances and the like.

Typical examples of the form of the TNFR2 expression-inducing composition (TNFR2 expression-inducing agent) include liquid formulas, suspensions, emulsions, aerosols, foams, granules, powders, tablets, capsules, ointments, aqueous gels and the like. For injection, etc., it may be formulated as a freeze-dried product or pellets to prepare a drug solution by dissolving it in saline or a suitable buffer (e.g., PBS) just prior to use.

The process itself of preparing a composition (drug) in various forms with the TNFR2 expression-inducing peptide (primary ingredient) and various carriers (secondary ingredients) may be carried out in accordance with a heretofore known method. Because such a preparation process itself is not distinctive to the present invention, detailed description is omitted. The detail information regarding formulations can be found in, for example, Comprehensive Medicinal Chemistry, edited by Corwin Hansch and published by Pergamon Press (1990). The entire contents of this book are incorporated in this description by reference.

The target cells to which the TNFR2 expression-inducing compound (TNFR2 expression-inducing peptide) disclosed herein is applied are not particularly limited as long as the cells are potentially capable of expressing TNF receptor 2. For instance, it can be applied also to undifferentiated cells that can be induced to differentiate into such cells. Alternatively, they can be primary cultured cells isolated from various organisms, or cells of a neoplastic or immortal cell line. The application target includes various organisms (typically humans or mammals other than humans). From the medical standpoint, it is preferably applied to immune cells or tissue in particular. This type of cells include macrophages, monocytes, various types of thymus cells (lymphocytes) such as natural killer cells and killer T cells, B cells, dendritic cells, hematopoietic stem cells, etc. Other preferable target TNFR2-expressing cells include adipose tissue, muscle tissue (including hearts) and cells constituting neural networks as well. The neural cells preferably include central nerve cells such as neurons and glia cells, etc., and neuroblastomas such as neuro-2a, N1E-115, etc. Not limited to these, various neurotransmitter cells can be used. The neurotransmitter activity can be detected by the patch clamp technique.

From the standpoint of treating diseases and disorders, stem cells are especially preferred as the target. Examples of cells of this type include embryotic stem cells, induced pluripotent stem cells (iPS cells), mesenchymal stem cells, neural stem cells, myeloid stem cells, hematopoietic stem cells, and the like. In particular, it can be preferably applied to undifferentiated stem cells (stem cells with no prior history of differentiation-inducing treatment).

The TNFR2 expression-inducing composition disclosed herein can be used according to a method and dosage appropriate for the form and purpose.

For example, with respect to cells (a cell mass), tissue, or an organ under in vitro incubation, a suitable amount of the TNFR2 expression-inducing composition (i.e., a suitable amount of a TNFR2 expression-inducing peptide) can be supplied to a culture medium containing the target cells (tissue).

The amount and the number of portions to be added are not particularly limited as they may vary in accordance with the conditions such as the type of cultured cells, cell density (initial cell density at the incubation start), passage number, incubation conditions, type of culture medium, etc. When mammalian cells are cultured, it can be added in one to several portions so that the concentration of the TNFR2 expression-inducing peptide in the culture medium is within a range of about 0.1 µM to 100 µM or more preferably within a range of 0.5 µM to 20 µM (e.g., 1 µM to 10 µM).

By supplying the TNFR2 expression-inducing composition (TNFR2 expression-inducing peptide) disclosed herein to an in vitro culture system, the target cells that express TNFR2 selectively (specifically or preferentially) can be efficiently produced.

Alternatively, when selective expression (or enhanced expression) of TNFR2 is induced in vivo in prescribed target TNFR2-expressing cells (a tissue fragment or a cell mass transplanted to a certain site), an appropriate amount of the TNFR2 expression-inducing composition (i.e., TNFR2 expression-inducing peptide) disclosed herein can be prepared into a liquid formula and administered in a desirable amount to the patient (i.e. in vivo) by intravenous, intramuscular, subcutaneous, intradermal, or intraperitoneal injection. Alternatively, it can be administered directly to the prescribed tissue (i.e., cells constituting the tissue) in a solid form such as tablets, in a gel form such as ointment, etc., or in an aqueous gel form. The amount and the number of portions to be added are not particularly limited as they may vary depending on conditions such as the type of cells to be induced for high TNFR2 expression, location, etc.

Several worked examples relating to the present invention are described below while these examples are not intended to limit the scope of the invention.

Example 1

Peptide Synthesis

In total, 19 different synthetic peptides consisting of the respective amino acid sequences of SEQ ID NOs: 1 to 19 listed in Table 1 were produced using a peptide synthesizer described later. In the following description, the 19 peptide species synthesized in total are referred to as Samples 1 to 19 corresponding to SEQ ID NOs: 1 to 19.

Each sample is constituted to have the amino acid sequence of one of the NoLS and NLS listed in Table 1 (as well as in Sequence Listing), and is a chemically synthesized linear peptide consisting entirely of at most 20 (specifically 7 to 19) amino acid residues. In the peptides of Samples 15 and 16, some (threonine residues) of the amino acid residues are phosphorylated. In each sample, the carboxyl group (—COOH) of the C-terminal amino acid is amidated (—CONH$_2$). All peptides were synthesized by solid-phase synthesis (Fmoc chemistry) using a commercial peptide synthesizer (an Intavis AG system) in accordance with the operation manual. Because the mode of using the peptide synthesizer itself is not distinctive to the present invention, detailed description is omitted.

Each sample synthesized was dissolved in PBS (phosphate buffered saline) to prepare a stock solution having a peptide concentration of 1 mM.

Example 2

Test of Each Synthetic Peptide for TNFR2 Expression-Inducing Activity Against Thymus Cells With respect to each sample obtained in Example 1, the TNFR2 expression-inducing activity was tested against thymus cells. The control group was supplied with no peptides. The test details are described below.

In a clean bench, rat thymus cells obtained beforehand were ground with two flame-sterilized glass slides. The ground cell mass (i.e., cell lump primarily comprising thymus cells) was suspended in a commercial RPMI-1640 medium, and the cells were dispersed by appropriate pipetting. Subsequently, the suspension was centrifuged to precipitate and collect the thymus cells (lymphocytes) dispersed in the culture medium.

In each test, 1.8 cm$^3$ of the culture medium was added to each well of a 24-well(hole) flat bottom cell culture plate to 6×10$^6$ cells per well. Subsequently, the stock solution of one of the samples was added to wells for each sample group to a peptide concentration in each well of 2 µM. Wells containing no added samples, but only the cell-containing culture medium were designated as the control group.

After samples (synthetic peptides) were added as described above, the cell culture plate was set still in a $CO_2$ incubator at 37° C. and 5% $CO_2$. After one hour incubation in the incubator, a cell staining test was performed. In particular, cultured cells in the wells for each sample group and the control group were subjected to nuclear staining by DAPI (4',6-diamidino-2-phenylindole) and observed under a fluorescent microscope. In addition, the same samples were evaluated for the expression/induction of TNFR1 and TNFR2 using an anti-TNFR1 polyclonal antibody and an anti-TNFR2 polyclonal antibody.

In particular, as the anti-TNFR1 polyclonal antibody binding specifically to the TNFR1 (TNF receptor 1 with 55 kDa MW) expressed by the cultured cell, was used a rabbit polyclonal TNFR1 antibody (product name: H-271, binding to an epitope with amino acids 30-301 of the extracellular domain of TNFR1 of human origin) available from Santa Cruz Biotechnology, Inc. As the anti-TNFR2 polyclonal antibody binding specifically to the TNFR2 (TNF receptor 2 with 75 kDa MW) expressed by the cultured cell, was used a goat polyclonal TNFR2 antibody (product name: L-20, binding to an epitope at the C-terminus of TNFR2 of mouse origin) available from Santa Cruz Biotechnology, Inc. The levels of TNFR1 expression and TNFR2 expression were then assessed by a fluorescent antibody technique using fluorescently labeled anti-rabbit IgG antibody and anti-goat IgG antibody as the secondary antibodies binding to these two different primary antibodies, respectively.

Figure 2:
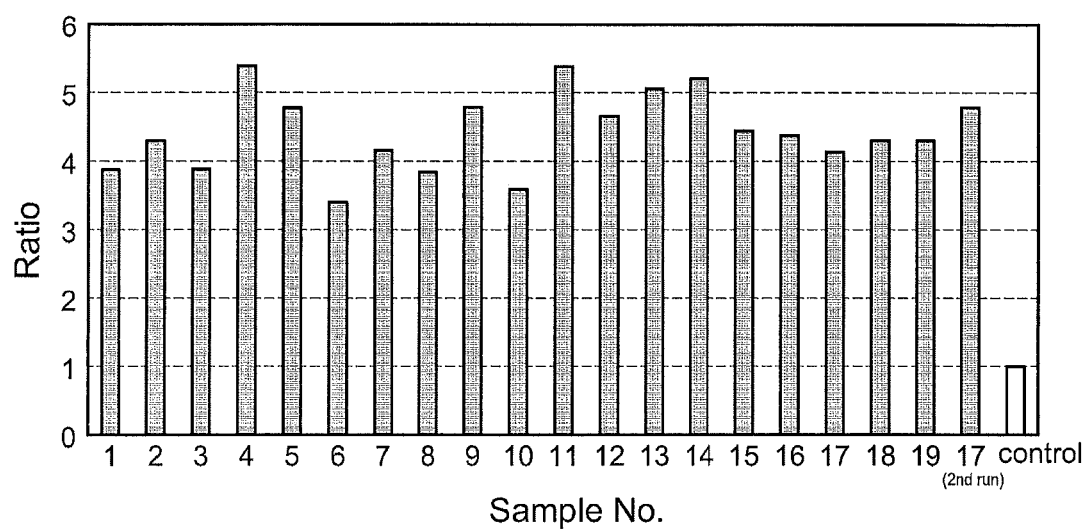
FIG. 2 shows a graph plotting the results of testing cultured cells of a control and each sample group for the TNFR2 expression levels (relative fluorescence intensity values with the control set as 1) based on a fluorescent antibody technique using an anti-TNFR2 polyclonal antibody (primary antibody) and a fluorescently labeled secondary antibody.

The results are shown in FIG. 1 and FIG. 2. FIG. 1 shows a graph plotting the results of testing cultured cells of the control group and each sample group for the TNFR1 expression levels based on the fluorescent antibody technique using the anti-TNFR1 polyclonal antibody (primary antibody) and fluorescently labeled secondary antibody. With the level of TNFR1 expression (i.e. fluorescence intensity) of the control group set as 1, relative values are shown. On the other hand, FIG. 2 shows a graph plotting the results of testing cultured cells of the control group and each sample group for the TNFR2 expression levels based on the fluorescent antibody technique using the anti-TNFR2 polyclonal antibody (primary antibody) and fluorescently labeled secondary antibody. With the level of TNFR2 expression (i.e. fluorescence intensity) of the control group set as 1, relative values are shown.

Figure 3:
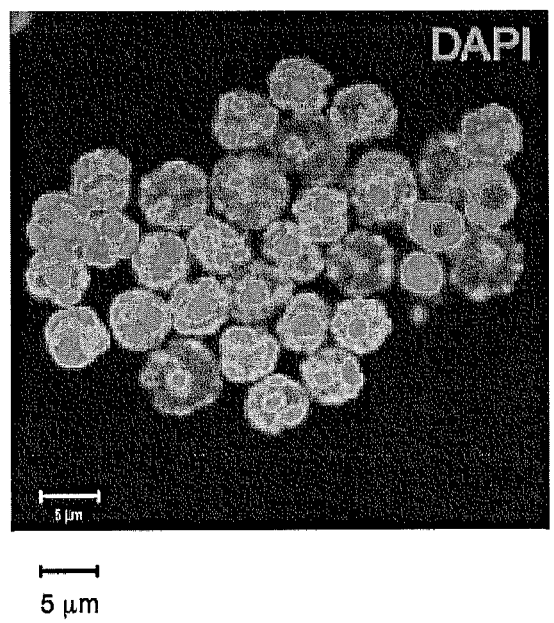
FIG. 3 shows a fluorescent microscope photo (image) of cultured cells of a control after staining with DAPI.
Figure 4:
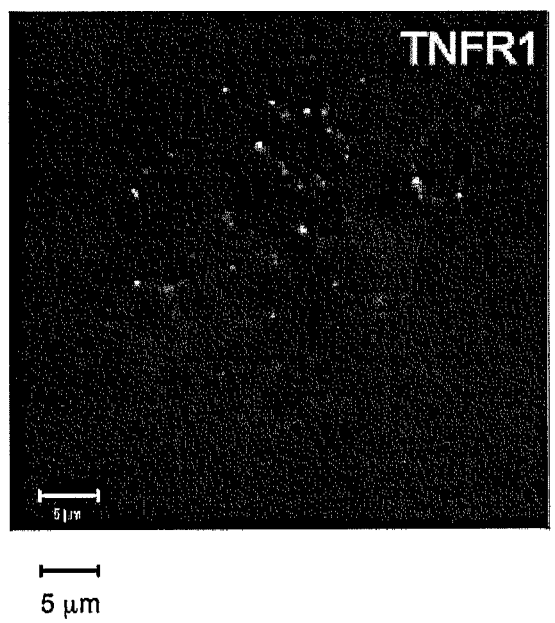
FIG. 4 shows a fluorescent microscope photo (image) showing the TNFR1 expression (presence) levels of cultured cells of a control based on a fluorescent antibody technique using an anti-TNFR1 antibody.
Figure 5:
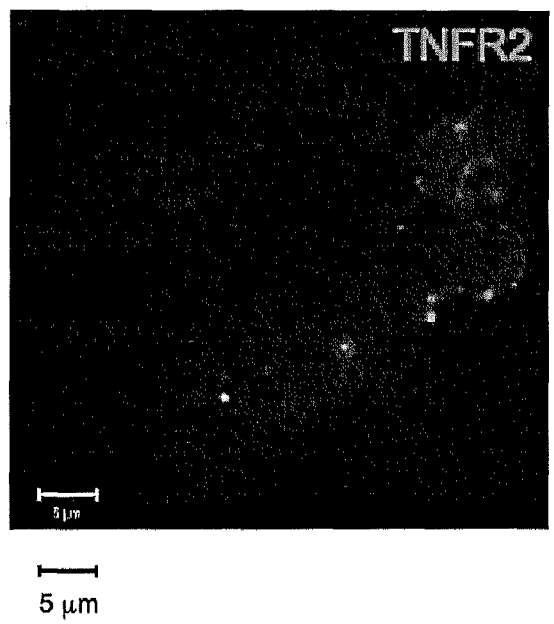
FIG. 5 shows a fluorescent microscope photo (image) showing the TNFR2 expression (presence) levels of cultured cells of a control based on a fluorescent antibody technique using an anti-TNFR2 antibody.

FIG. 3 to FIG. 5 show fluorescent microscope photos of cultured cells of the control group. FIG. 3 shows the results of DAPI staining. FIG. 4 shows the results based on the fluorescent antibody technique using the anti-TNFR1 antibody. FIG. 5 shows the results based on the fluorescent antibody technique using the anti-TNFR2 antibody.

Figure 6:
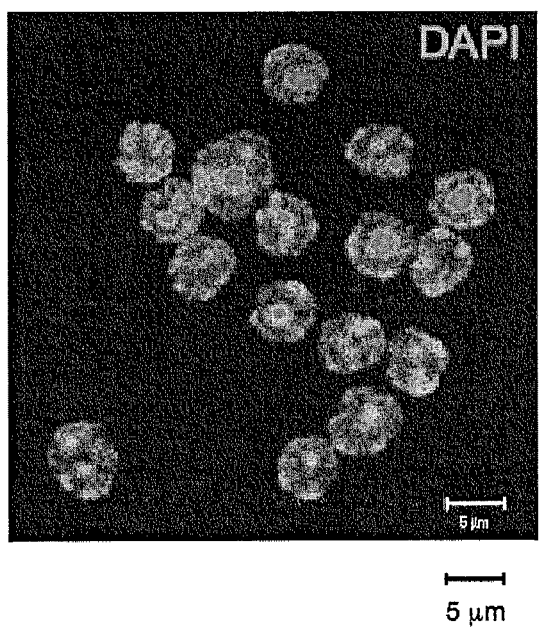
FIG. 6 shows a fluorescent microscope photo (image) of cells incubated with a sample (synthetic peptide) according to a worked example, taken after staining with DAPI.
Figure 7:
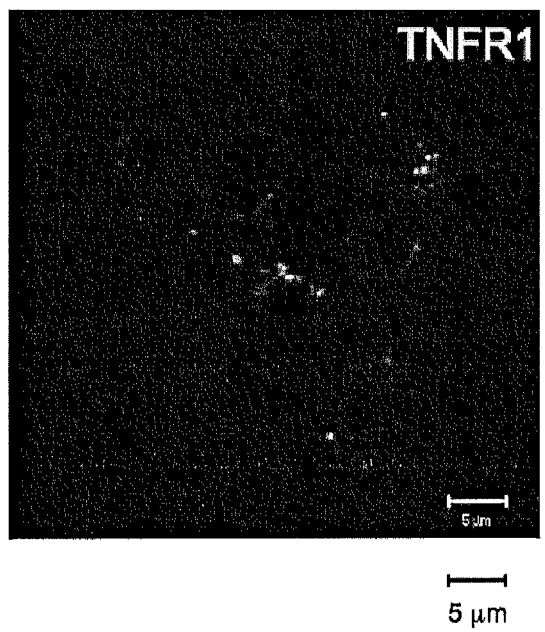
FIG. 7 shows a fluorescent microscope photo (image) showing the TNFR1 expression (presence) levels of cells incubated with a sample (synthetic peptide) according to a worked example based on a fluorescent antibody technique using an anti-TNFR1 antibody.
Figure 8:
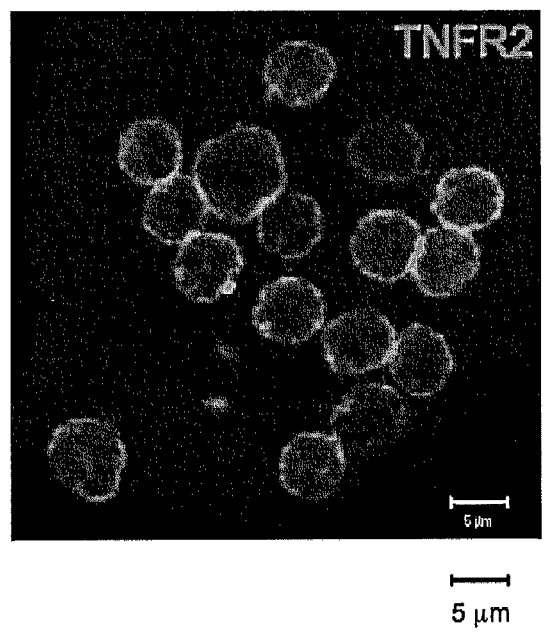
FIG. 8 shows a fluorescent microscope photo (image) showing the TNFR2 expression (presence) levels of cells incubated with a sample (synthetic peptide) according to a worked example based on a fluorescent antibody technique using an anti-TNFR2 antibody.

FIG. 6 to FIG. 8 show fluorescent microscope photos of cultured cells incubated with Sample 17 making use of the peptide of SEQ ID NO: 17. FIG. 6 shows the results of DAPI staining. FIG. 7 shows the results based on the fluorescent antibody technique using the anti-TNFR1 antibody. FIG. 8 shows the results based on the fluorescent antibody technique using the anti-TNFR2 antibody. It is noted that for the Sample 17 group, the test was repeated twice, independently from each other, and the fluorescent microscope photo shown was taken of the second run for the Sample 17 group (of the one indicated as Sample 17 ($2^{nd}$ run) in FIG. 1 and FIG. 2).

As evident from the results shown in FIG. 1 and FIG. 2 as well as FIG. 3 to FIG. 8, each sample group incubated with one of the samples (i.e. TNFR2 expression-inducing peptides) disclosed herein showed a high level of TNFR2 expression (induction), with the relative fluorescence intensity being at least 3 (typically at least 4, especially preferably at least 5) up to 6 as compared to the control group. On the other hand, with respect to the TNFR1 expression, none of the sample groups showed a significant difference from the control group, indicating that the TNFR1 expression was not enhanced (induced) with addition of any sample.

This indicates that each peptide synthesized for each sample is a TNFR2 expression-inducing peptide capable of inducing selective expression of TNFR2 between TNFR1 and TNFR2 when supplied to prescribed cells (i.e., target TNFR2-expressing cells), suggesting its usability as an active ingredient in a composition to induce specific expression of TNFR2 in target TNFR2-expressing cells.

Example 3

Test of Each Synthetic Peptide for TNFR2 Expression-Inducing Activity Against Neuroblasts With respect to each sample obtained in Example 1, the TNFR2 expression-inducing activity was tested against neuroblasts. The control group was supplied with no peptides. The test details are described below.

As the cells under test, a cell line (neuro-2a) established from a commercial mouse neuroblastoma was used. The cells were cultured beforehand in a DMEM medium (i.e., a Dulbecco MEM (DMEM medium, a Gibco product) containing 10% fetal bovine serum (FBS, a Gibco product), 2 mM of L-glutamine, 50 unit/mL of penicillin, and 50 µg/mL of streptomycin), and the number of cells per well in a 96-hole(well) plate was adjusted to approximately $5 \times 10^3$. The volume of the medium here was 100 µL/well. To this, differentiation-inducing retinoic acid was administered at 20 µM per well, and allowed to act for about 168 hours (7 days) in a $CO_2$ incubator (37° C., 5% $CO_2$).

By this means, neuritis of the neuro-2a cells were elongated and differentiated into neuron-like cells.

Subsequently, the stock solution of one of the samples was added to the wells for each sample group to a peptide concentration in each well of 5 µM. Wells containing no added samples, but only the cell-containing culture medium were designated as the control group. After samples (synthetic peptides) were added as described above and continuously incubated further for two days, the expression/induction of TNFR1 and TNFR2 was evaluated according to the fluorescent antibody technique in the same manner as Example 2.

Figure 9:
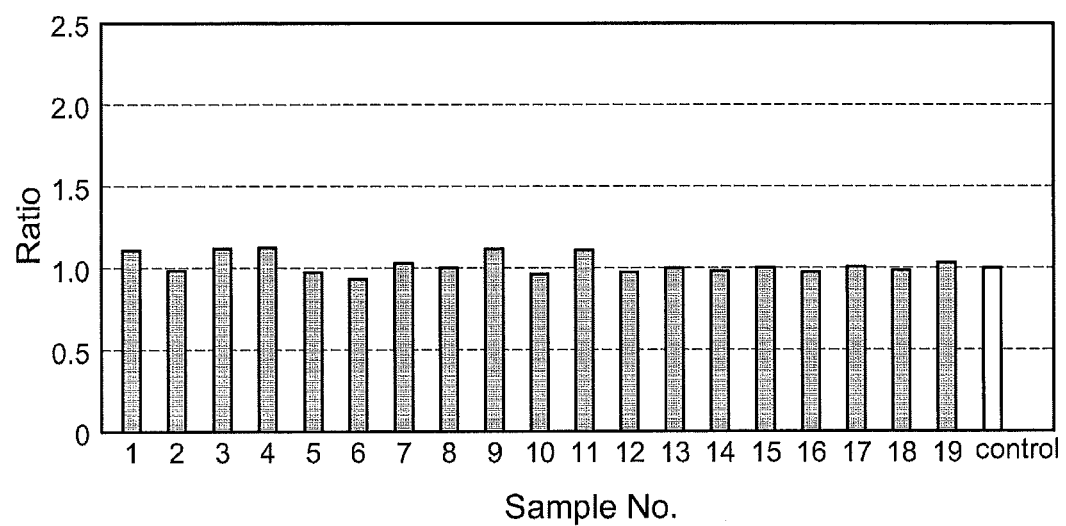
FIG. 9 shows a graph plotting the results of testing cultured cells of a control and each sample group for the TNFR1 expression levels (relative fluorescence intensity values with the control set as 1) based on a fluorescent antibody technique using an anti-TNFR1 polyclonal antibody (primary antibody) and a fluorescently labeled secondary antibody.
Figure 10:
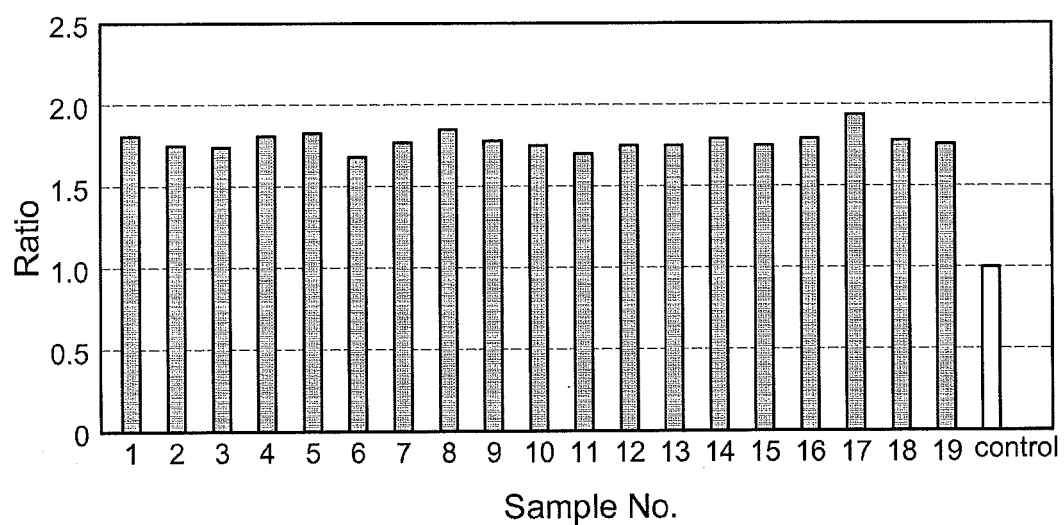
FIG. 10 shows a graph plotting the results of testing cultured cells of a control and each sample group for the TNFR2 expression levels (relative fluorescence intensity values with the control set as 1) based on a fluorescent antibody technique using an anti-TNFR2 polyclonal antibody (primary antibody) and a fluorescently labeled secondary antibody.

The results are shown in FIG. 9 and FIG. 10. FIG. 9 shows a graph plotting the results of testing cultured cells of the control group and each sample group for the TNFR1 expression levels based on the fluorescent antibody technique using the anti-TNFR1 polyclonal antibody (primary antibody) and fluorescently labeled secondary antibody. With the level of TNFR1 expression (i.e. fluorescence intensity) of the control group set as 1, relative values are shown. On the other hand, FIG. 10 shows a graph plotting the results of testing cultured cells of the control group and each sample group for the TNFR2 expression levels based on the fluorescent antibody technique using the anti-TNFR2 polyclonal antibody (primary antibody) and fluorescently labeled secondary antibody. With the level of TNFR2 expression (i.e. fluorescence intensity) of the control group set as 1, relative values are shown.

As evident from the results shown in FIG. 9 and FIG. 10, each sample group incubated with one of the samples (i.e. TNFR2 expression-inducing peptides) disclosed herein showed a high level of TNFR2 expression (induction), with the relative fluorescence intensity being at least 1.5 (typically at least 1.6, especially preferably at least 1.8) up to 2.0 as compared to the control group. Especially, the amino acid sequence of SEQ ID NO: 17 showed fluorescence intensity as significantly high as at least 1.9 relative to the control group. On the other hand, with respect to the TNFR1 expression, none of the sample groups showed a significant difference from the control group, indicating that the TNFR1 expression was neither stimulated nor enhanced (induced) with addition of any sample.

This indicates that each peptide synthesized for each sample is a TNFR2 expression-inducing peptide capable of inducing selective expression of TNFR2 between TNFR1 and TNFR2 when supplied to prescribed cells (i.e., target TNFR2-expressing cells), suggesting its usability as an active ingredient in a composition to induce specific expression of TNFR2 in target TNFR2-expressing cells.

Example 4

Preparation of Granular Formulation 50 mg of Sample 17 peptide was mixed with 50 mg of crystallized cellulose and 400 mg of lactose. 1 mL of an ethanol-water solution was added thereto and the resultant was mixed well. The resulting mixture was prepared into granules according to a conventional method to obtain a granular formulation containing a TNFR2 expression-inducing peptide disclosed herein (i.e., a TNFR2 expression-inducing composition in granules) as the primary ingredient.

INDUSTRIAL APPLICABILITY

As described above, the TNFR2 expression-inducing peptide disclosed herein is highly capable of inducing TNFR2 expression; and therefore, a TNFR2 expression-inducing composition (pharmaceutical composition) containing the peptide can be used as a research reagent or a medical drug (composition) to induce selective (specific) TNFR2 expression in prescribed cells. By use of the composition, a method for producing cells expressing TNFR2 selectively between TNFR1 and TNFR2 is provided.

[Sequence Listing Free Text]

SEQ ID NOs: 15, 16 phosphorylated

The invention claimed is:

1. A method for producing cells that express TNF receptor 2 selectively between TNF receptor 1 (TNFR1) and TNF receptor 2 (TNFR2), the production method comprising:
   preparing an artificially synthesized C-terminal amidated peptide consisting of an amino acid sequence of any one of SEQ ID NOs: 1 to 51;
   culturing at least one species of immune cells in a culture medium;
   supplying the artificially synthesized C-terminal amidated peptide to the medium including the immune cells; and
   further culturing the immune cells in the medium containing the artificially synthesized C-terminal amidated peptide to enhance expression of TNFR2 selectively between TNFR1 and TNFR2 in the cells.

2. The production method according to claim 1, wherein the immune cells are derived from the thymus.

3. The production method according to claim 1, wherein the immune cells are selected from the group consisting of macrophages, monocytes, lymphocytes, B cells, dendritic cells and hematopoietic stem cells.

4. The production method according to claim 1, wherein the artificially synthesized peptide consists of an amino acid sequence of any one of SEQ ID NOs: 1 to 19.

* * * * *